US011986544B2

(12) United States Patent
Perez et al.

(10) Patent No.: US 11,986,544 B2
(45) Date of Patent: May 21, 2024

(54) APPLICATION FOR INHIBITORS OF cAMP EFFLUX IN BODY CARE

(71) Applicant: UNM RAINFOREST INNOVATIONS, Albuquerque, NM (US)

(72) Inventors: Dominique Renee Perez, Albuquerque, NM (US); Larry A. Sklar, Albuquerque, NM (US); Alexandre Chigaev, Santa Fe, NM (US)

(73) Assignee: UNM RAINFOREST INNOVATIONS, Albuquerque, NM (US)

( * ) Notice: Subject to any disclaimer, the term of this patent is extended or adjusted under 35 U.S.C. 154(b) by 123 days.

(21) Appl. No.: 17/438,362

(22) PCT Filed: Mar. 10, 2020

(86) PCT No.: PCT/US2020/021838
§ 371 (c)(1),
(2) Date: Sep. 10, 2021

(87) PCT Pub. No.: WO2020/185746
PCT Pub. Date: Sep. 17, 2020

(65) Prior Publication Data

US 2022/0183945 A1 Jun. 16, 2022

Related U.S. Application Data

(60) Provisional application No. 62/816,415, filed on Mar. 11, 2019.

(51) Int. Cl.

| | |
|---|---|
| ***A61K 8/49*** | (2006.01) |
| ***A61Q 15/00*** | (2006.01) |
| ***A61Q 19/00*** | (2006.01) |

(52) U.S. Cl.
CPC .............. *A61K 8/498* (2013.01); *A61Q 15/00* (2013.01); *A61Q 19/00* (2013.01)

(58) Field of Classification Search
None
See application file for complete search history.

(56) References Cited

U.S. PATENT DOCUMENTS

| | | | | |
|---|---|---|---|---|
| 9,314,460 | B1 | 4/2016 | Chigaev et al. | |
| 10,039,771 | B2 | 8/2018 | Chigaev et al. | |
| 2007/0269537 | A1 * | 11/2007 | Gupta | A61P 17/10 514/450 |

OTHER PUBLICATIONS

Perez D, et al. A High-Throughput Flow Cytometry Assay for Identification of Inhibitors of 3',5'-Cyclic Adenosine Monophosphate Efflux. Methods Mol Biol, 2016;1439:227-244.

(Continued)

*Primary Examiner* — Kyung S Chang
(74) *Attorney, Agent, or Firm* — Henry D. Coleman; R. Neil Sudol

(57) ABSTRACT

The present invention is directed to previously identified inhibitors of cAMP efflux (ICE) and their use in treating/masking body odor, inhibiting, reducing and/or eliminating hyperhidrosis (excessive sweating), tanning skin or protecting skin before and/or after exposure to the sun as well as for treating certain skin conditions, in one embodiment, the invention provides a method for inhibiting body odor, a condition that is characterized by an unpleasant odor from the products of the microbial sweat degradation. By inhibiting the efflux of the precursor compounds that are degraded, novel compounds are capable of preventing unwanted odors. Deodorant compositions that employ this new approach for the control of bodily odor are provided, ICE compounds can also be used as components, of cosmetic formulations including tanning and after-sun formu- (Continued)

lations, formulations for skin conditions as described herein and other cosmetic formulations.

4 Claims, 1 Drawing Sheet

(56) References Cited

OTHER PUBLICATIONS

Perez DR, et al. Cyclic AMP efflux inhibitors as potential therapeutic agents for leukemia. Oncotarget, 2016;7(23):33960-33982.
Rodriguez S, et al. Dependence of deodorant usage on ABCC11 genotype: scope for personalized genetics in personal hygiene. J Invest Dermatol, 2013;133(7):1760-1767.
Yoshiura K, et al. A SNP in the ABCC11 gene is the geterminant of human earwax type. Nat Genet, 2006;38 (3):324-330.
Nakano M, et al. A strong association of axillary osmidrosis with the wet earwax type determined by genotyping of the ABCC11 gene. BMC Genet, 2009;10:42.
Toyoda Y, et al. Earwax, osmidrosis, and breast cancer: why does one SNP (538G>A) in the human ABC transporter ABCC1 gene determine earwax type? FASEB J, 2009;23(6):2001-2013.
Guo Y, et al. MRP8, ATP-binding cassette C11 (ABCC11) is a cyclic nucleotide efflux pump and a resistance factor for fluoropyrimidines 2',3'-dideoxycytidine and 9'-(2'-phosphonylmethoxyethyl)adenine. J Biol Chem, 2003;278(32):29509-29514.
Endo C, et al. Genome-wide association study in Japanese females identifies fifteen novel skin-related trait associations. Sci Rep, 2018;8(1):8974.
D'Mello SA, et al. Signaling Pathways in Melanogenesis. Int J Mol Sci, 2016;17(7).
Spry ML, et al. Prolonged treatment of fair-skinned mice with topical forskolin causes persistent tanning and UV protection. Pigment Cell Melanoma Res, 2009;22(2):219-229.
Zhang X, et al. PDE5 inhibitor promotes melanin synthesis through the PKG pathway in B16 melanoma cells. J Cell Biochem, 2012;113(8):2738-2743.
Natale CA, et al. Sex steroids regulate skin pigmentation through nonclassical membrane-bound receptors. Elife, 2016;5.

* cited by examiner cAMP efflux validated hits
IC50 is shown next to the compound

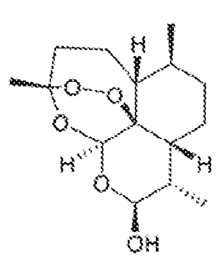

Dihydroartemisinin
$C_{16}H_{26}O_5$
Exact Mass: 298.18
Mol. Wt.: 298.37
C, 64.41; H, 8.78; O, 26.81

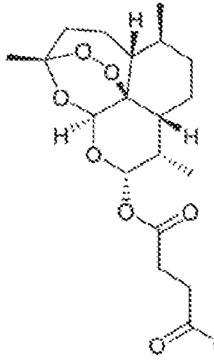

Artesunate
$C_{19}H_{28}O_8$
Exact Mass: 384.18
Mol. Wt.: 384.42
C, 59.36; H, 7.34; O, 33.30

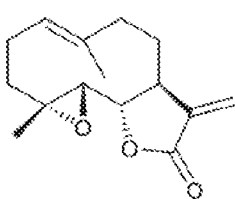

Parthenolide
$C_{15}H_{20}O_3$
Exact Mass: 248.14
Mol. Wt.: 248.32
C, 72.55; H, 8.12; O, 19.33

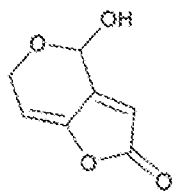

Patulin
$C_7H_6O_4$
Exact Mass: 154.03
Mol. Wt.: 154.12
C, 54.55; H, 3.92; O, 41.52

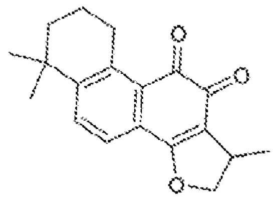

Cryptotanshinone
$C_{19}H_{20}O_3$
Exact Mass: 296.14
Mol. Wt.: 296.36
C, 77.00; H, 6.80; O, 16.20

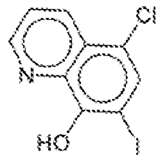

Clioquinol
$C_9H_5ClINO$
Exact Mass: 304.91
Mol. Wt.: 305.50
C, 35.38; H, 1.65; Cl, 11.60; I, 41.54; N, 4.58; O, 5.24

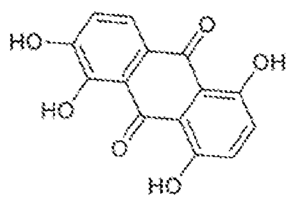

Quinalizarin
$C_{14}H_8O_6$
Exact Mass: 272.03
Mol. Wt.: 272.21
C, 61.77; H, 2.96; O, 35.27

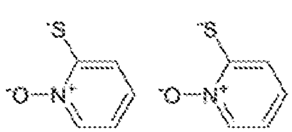

$Zn^{++}$

1-Hydroxypyridine 2-thione Zn
$C_{10}H_8N_2O_2S_2Zn$
Exact Mass: 315.93
Mol. Wt.: 317.70
C, 37.80; H, 2.54; N, 8.82; O, 10.07; S, 20.19; Zn, 20.58

APPLICATION FOR INHIBITORS OF cAMP EFFLUX IN BODY CARE

RELATED APPLICATIONS

This application is a United States national phase patent application based upon international patent application number PCT/US20/21838 of international filing date Mar. 10, 2020, which claims the benefit of priority of United States provisional application serial no U.S. 62/816,415, filed Mar. 11, 2019, of identical title, the entire contents of said application being incorporated by reference in its entirety herein.

FIELD OF THE INVENTION

The present invention is directed to cosmetic compositions, especially deodorant compositions, tanning and after-sun formulations and compositions for treating certain skin disorders. These compositions include an effective amount of at least one inhibitor of cAMP efflux, in combination with cosmetic additives and ingredients as otherwise described herein. Methods of treating/masking body odor, inhibiting, reducing and/or eliminating hyperhidrosis (excessive sweating), tanning skin or protecting skin before and/or after exposure to the sun as well as cosmetic formulations, including formulations for treating certain skin conditions represent embodiments of the present invention.

BACKGROUND AND OVERVIEW OF THE INVENTION

Existing deodorants, compounds and formulations applied to human skin that decrease, eliminate or mask natural body odors can be classified into two major groups: 1) natural or artificial fragrances that mask undesirable odors by offering a more desirable alternative, and 2) antimicrobial compounds that prevent the development of bacteria converting sweat compounds, which normally lack any smell, into malodorous substances. Antiperspirants, formulations that inhibit or decrease sweat production can also decrease unwanted odors through a different mechanism.

Odor-producing glands, that in humans are termed apocrine glands, do not produce a large amount of sweat or contribute to body thermoregulation. Instead, they are specialized for the excretion of specific odorous compounds that in lower mammals function as pheromones, compounds that attract the opposite sex. In humans, some of these odors are perceived as unpleasant. Apocrine glands are localized on the axillae (under-arm area), in the genital area and the abdomen. Protein transporters, responsible for the efflux of compounds in apocrine glands, and specifically the transporter termed ABCC11, are also capable of the efflux of cyclic nucleotides, including cAMP.

Accordingly, the present invention is directed to the discovery that newly identified inhibitors of cAMP efflux (ICE) can be used in: 1) deodorant formulations to mask odors; 2) tanning formulations 3) after-sun cosmetic formulations to protect the skin from sunburn; as components of: 4) cosmetic formulations and 5) in formulations for "unhappy skin" conditions, not intended to treat any specific disease or disorder.

Several ICE compounds identified in screens, including artemisinin and its derivatives, parthenolide, patulin, crypthotanshinone [1-4] represent natural plant-source substances that can be produced organically. Others represent off-patent drugs that were reported to be used in topical formulation for treatment of skin diseases and therefore, are safe and previously tested in humans. According to our preliminary analysis, none of these substances has been previously used as components of deodorants or other formulations as described herein.

In another embodiment, the present invention relates to cosmetic (preferably, topical) compositions comprising an effective amount of at least one cAMP efflux inhibitor compound as otherwise described herein in combination with at least one additional cosmetic additive selected from: water, a water compatible cosmetically acceptable solvent such as alcohol, a water incompatible solvent, emollients, humectants, oils (polar and non-polar which may provide oil-in-water or water-in-oil emulsions, an essential oil such as lavender, melaleuca, peppermint, frankincense, among others), conditioning agents, surfactants, thickeners/thickening agents, stiffening agents, emulsifiers, medicaments, fragrances, preservatives, deodorant components, antiperspirant compounds, skin protecting agents, including sunscreen agents, pigments, dyes, coloring agents, preservatives and mixtures thereof, among others. Compositions according to the present invention also optionally include an additional bioactive agent, such as an anti-acne compound (e.g. peroxides such as hydrogen peroxide and benzoyl peroxide, dialkyl peroxides, peresters, inorganic peroxides, percarbonates, triclosan, quaternary compounds, retinoids such as adapalene, isotretinoin, tretinoin, pharmaceutically acceptable salts and esters thereof and the like and mixtures thereof, among others), a traditional deodorant compound such as triclosan or a cyclomethicone or a mixture thereof, an antiperspirant compound such as an antiperspirant aluminum salt (e.g., aluminum chlorhydrate, aluminum formate, aluminum zirconium tetrachlorhydrex glycine or a mixture thereof), vitamin C, vitamin E, vitamin A, coenzyme Q, *Aloe vera* and other agents which are useful to enhance the appearance of skin. In certain embodiments, cosmetic compositions comprise at least two of the above-described compounds.

All components which are included in compositions according to the present invention are cosmetically compatible and are components readily recognized by skilled practitioners in the art.

Methods according to the present invention relate to the inhibition, resolution or reducing the likelihood of body malodor, reducing, inhibiting and/or eliminating hyperhidrosis, enhancing skin tanning protecting skin before and/or after sun exposure and treating (including reducing) and/or resolving various skin conditions including wrinkles, cellulite, scarring, rashes, itching skin, swelling, redness, flaky dry skin, repairing damaged skin, smoothing rough skin, calluses, reducing and/or eliminating skin imperfections (including resolving bumps and/or acne in skin) and naturalizing skin color to its original condition (especially including reversing whitening/lightening of skin). In this method embodiment, at least one cAMP inhibitor in an effective amount is administered to the subject, often in topical dosage form to the tissue to be treated (other mutes of administration are also intended and contemplated), for the purpose of providing an intended effect on the skin or other keratinous tissue of the subject. A more detailed description of the invention follows.

DESCRIPTION OF THE FIGURES

FIG. 1 shows exemplary preferred compounds for use in the present invention. These compounds include dihydroartemisinin, artesunate, parthenolide, patulin, cryptotanshinone, clioquinol, quinalizarin, 1-hydroxypyridine-2-thione zinc and pharmaceutically acceptable salts and alternative salts thereof. Other compounds for use in the present invention are as otherwise described herein.

DETAILED DESCRIPTION OF THE INVENTION

Unless otherwise specified, "a," "an," "the," and "at least one" are used interchangeably and mean one or more than one, depending on the context of use.

The following terms shall be used to describe the present invention. In instances where a term is not defined herein, such term is given its common meaning by those of ordinary skill in the art.

The term "patient" or "subject" refers to a mammal, preferably a human, including a domesticated mammal (including a dog, cat, sheep, horse, cow, pig, goat or other domesticated mammal) in need of treatment or therapy to which compounds according to the present invention are administered in order to treat a condition or disease state otherwise described herein.

The term "compound", as used herein, unless otherwise indicated, refers to any specific chemical compound disclosed herein and includes within context, tautomers, regioisomers, geometric isomers, and where applicable, optical isomers thereof where applicable, as well as pharmaceutically acceptable salts, solvates and polymorphs thereof. Within its use in context, the term compound generally refers to a single compound, but also may include other compounds such as stereoisomers, regioisomers and/or optical isomers (including in some instances, racemic mixtures) as well as specific enantiomers or enantiomerically enriched mixtures of disclosed compounds. The compounds of this invention include all pharmaceutically acceptable salt forms, solvates, polymorphs and prodrug forms of the present compounds, where applicable.

The term "modulate" means, with respect to disease states or conditions, modulated through (e.g, by binding) or having an effect on/inhibit cAMP efflux to produce, either directly or indirectly, an improvement or lessening of a condition or disease state which was, prior to administration of a compound according to the present invention, sub-optimal and in many cases, debilitating. While not being limited by way of theory, it is believed that modulation, at least with respect to the deodorant effect that the present invention provides, occurs by inhibition of cAMP efflux/ABC11 transporter and/or activity from apocrine glands in the subject. In most/many instances, the term modulate shall mean direct or indirect inhibition of cAMP efflux/ABCC11 transporter either alone or within the context of treating a condition such as body malodor, hyperhidrosis, enhancing tanning and/or providing a skin protective effect after a subject's skin has been exposed to the sun or for providing a cosmetic improvement to skin and nails as otherwise described herein.

The following compounds find use as cAMP efflux inhibitors in the present invention, all used in effective amounts: Bepridil, lidoflazine, nicardipine, propafenone, rescinnamine, GBR 12909, ellipticine, hexestrol, ketoconazole, cyclosporine A, loxapine, pimozide, acacetin, mometasone furoate, its active 6β-hydroxy metabolite, valspodar, tariquidar, elacridar, zosuquidar, MK571, XR9051, verapamil, dofequidar, reversan, biricodar, nicardipine, the *Aspergillus fumigatus* mycotoxin fumitremorgin C (12α-Fumitremorgin C or FTC) or its analogs Ko-32, Ko-134, and Ko-143, artemisinin, artemether, artesunate, dihydroartemisinin, patulin, 1-hydroxypyridine-2-thione zinc salt (pyrithione zinc), parthenolide, quinalizarin, clioquinol, cryptotanshinone, harmalol, a compound according to the chemical structure:

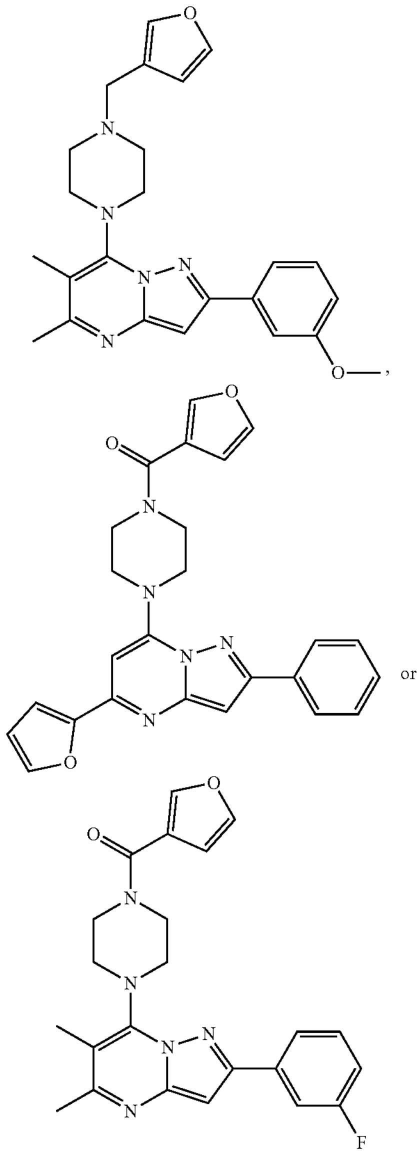

or a pharmaceutically acceptable salt or stereoisomer thereof, or a mixture thereof. Preferred compounds for use in the present invention am the compounds dihydroartemisinin, artesunate, parthenolide, patulin, cryptotanshinone, clioquinol, quinalizarin, 1-hydroxypyridine-2-thione zinc and pharmaceutically acceptable salts and alternative salts thereof.

The term "independently" is used herein to indicate that the variable, which is independently applied, varies independently from application to application.

The term "cosmetic condition" is used to describe distressed states or conditions of the skin and nails which are enhanced, treated, inhibited or resolved, by one or more compositions according to the present invention which include compounds as described herein which modulate and in particular inhibit cAMP efflux such that compounds which inhibit cAMP efflux may be used to treat these distressed states and/or conditions. These distressed states and/or conditions include, for example, wrinkles, cellulite, scarring, rashes, itching skin, swelling, redness, flaky dry skin, repairing damaged skin, smoothing rough skin, reducing and/or eliminating skin imperfections (including resolving bumps in skin) and naturalizing skin color to its original condition (especially including reversing whitening of skin). Compositions for use in the present invention are particularly useful for rejuvenating and beautifying keratinous tissue, especially skin tissue (enhancing the appearance and/or feel of the skin).

The ten "tanning" is used to describe the darkening of the skin, principally by enhancing melanin production in the subject upon exposure to the sun. Compositions according to the present invention increase tanning (melanogenesis) without exposure to UV light and can be used favorably in tanning applications which avoid UV light exposure. Compositions according to the present invention may favorably protect skin against UV light exposure by enhancing melanogenesis before, during and/or after exposure of the subject's skin to the sun by providing an enhanced effect on melanogenesis.

The term "body malodor" is used to describe an odor produced by the apocrine glands of a subject. While apocrine glands are activated as part of the body's cooling system, apocrine glands can produce and excrete specific compounds that are odorous in nature. These odors are often perceived as unpleasant. Apocrine glands are localized on the axillae (under-arm area), in the genital area and the abdomen. Protein transporters, responsible for the efflux of these compounds in apocrine glands, and specifically the transporter termed ABCC11 are also capable of the efflux of cyclic nucleotides, including cAMP. By inhibiting cAMP efflux, compounds which are used pursuant to the present invention function as a deodorant by inhibiting the efflux of odorous compounds from the subject's apocrine glands.

The term "co-administration" or "combination therapy" is used to describe a therapy in which at least two active compounds in effective amounts are used to treat a disease state or condition as otherwise described herein at the same time. This term includes the administration of an anti-acne compound (e.g. peroxides such as hydrogen peroxide and benzoyl peroxide, dialkyl peroxides, peresters, inorganic peroxides, percarbonates, triclosan, quaternary compounds, retinoids such as adapalene, isotretinoin, tretinoin, pharmaceutically acceptable salts and esters thereof and the like and mixtures thereof, among others), vitamin C, vitamin E, vitamin A, coenzyme Q, *Aloe vera* and other agents which are useful to enhance the appearance of skin along with cosmetic compositions according to the present invention. Co-administration can occur by the additional agent being incorporated into the cosmetic composition or simply being co-administered along with the composition. Although the term co-administration preferably includes the administration of two active compounds to the patient at the same time, it is not necessary that the compounds be administered to the patient at the same time, although effective amounts of the individual compounds will be present in the patient at the same time to effect an intended result. In certain aspects of the invention, one or more compounds according to the present invention may be administered with, for example, an anti-acne compound (e.g. peroxides such as hydrogen peroxide and benzoyl peroxide, dialkyl peroxides, peresters, inorganic peroxides, percarbonates, triclosan, quaternary compounds, retinoids such as adapalene, isotretinoin, tretinoin, pharmaceutically acceptable salts and esters thereof and the like and mixtures thereof, among others), vitamin C, vitamin E, vitamin A, coenzyme Q, *Aloe vera* and other agents which are useful to enhance the appearance of skin along with cosmetic compositions according to the present invention. Co-administration of one of the present compounds with another agent as otherwise described herein will often result in an additive or synergistic enhancement of the activity of the other agent.

"Treat", "treating", and "treatment", etc., as used herein, refer to any action providing a benefit to a patient at risk for or afflicted with a skin or other condition (malodor, hyperhidrosis, etc.) as otherwise described herein, including improvement in the condition through lessening or suppression of at least one symptom, delay in progression of the condition, resolution and/or inhibition of the condition. These terms also refer to the treatment of skin to enhance tanning or to protect the skin during and/or after exposure to the sun.

"Pharmaceutically acceptable" or "cosmetically acceptable" as used herein means that the compound or composition is suitable for administration, preferably for topical application to a subject to achieve the treatments and/or benefits described herein, without unduly deleterious side effects in light of the severity of the conditions and necessity of the treatment. It is noted that the compositions described herein may also be formulated for administration by routes other than topical.

"Inhibit" as used herein refers to the partial or complete elimination of a potential effect, while inhibitors are compounds that have the ability to inhibit. "Resolve" as used herein refers to the substantial resolution, including a complete resolution of a condition to be treated.

The present invention includes the compositions comprising the pharmaceutically acceptable salt, i.e., the acid or base addition salts of compounds of the present invention and their derivatives, where applicable. The acids which may be used to prepare the pharmaceutically acceptable acid addition salts of the aforementioned base compounds useful in this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among others.

Pharmaceutically acceptable base addition salts may also be used to produce pharmaceutically acceptable salt forms of the compounds according to the present invention. The chemical bases that may be used as reagents to prepare pharmaceutically acceptable base salts of the present compounds that are acidic in nature are those that form non-toxic base salts with such compounds. Such non-toxic base salts include, but are not limited to, those derived from such pharmacologically acceptable cations such as alkali metal cations (e.g., potassium and sodium) and alkaline earth metal cations (i.e., calcium and magnesium), ammonium or water-soluble amine addition salts such as N-methylglucamine-(meglumine), and the lower alkanolammonium and other base salts of pharmaceutically acceptable organic amines, among others.

The term "rejuvenate" is used to describe damaged keratinous tissue, especially skin tissue, which has been improved to a more normal, natural state, including the appearance and feel of the tissue, especially including the elasticity, softness and moisturizing qualities of the tissue.

The term "beautify" refers to taking skin and enhancing its appearance and feel by exposing the skin to the compositions disclosed herein.

The term "additional agent" is used to describe an additional bioactive compound, which may be co-administered with one or more compounds in cosmetic compositions of the present invention in the treatment of skin, especially acne. Such agents include, for example, anti-acne agents (e.g. peroxides such as hydrogen peroxide and benzoyl peroxide, dialkyl peroxides, peresters, inorganic peroxides, percarbonates, triclosan, quaternary compounds, retinoids such as adapalene, isotretinoin, tretinoin, pharmaceutically acceptable salts and esters thereof and the like and mixtures thereof, among others), and other agents such as vitamin C, vitamin E, vitamin A, coenzyme Q, *Aloe vera* and other agents which are useful to enhance the appearance of skin.

Because of the activity exhibited by compounds according to the present invention, it has been discovered that these compounds may be used to treat numerous conditions of keratinous tissue in patients or subjects who suffer from those conditions or disease states or are at risk for those conditions. In this method at least one compound, alone or in further combination with at least one additional bioactive agent in an effective amount is administered to a patient in need of to treat or reduce the likelihood of the occurrence or worsening of the condition(s) or state(s) of the keratinous tissue. The compounds and methods of the invention are useful for treating, resolving, inhibiting and/or reducing the likelihood or worsening of any the following skin conditions. These disease states and/or conditions include for example, wrinkles, cellulite, scarring, rashes, itching skin, swelling, redness, flaky dry skin, repairing damaged skin, smoothing rough skin, calluses, reducing and/or eliminating skin imperfections (including resolving bumps in skin) and naturalizing skin color to its original condition (especially including reversing whitening of skin) and reversing the effects of damaged skin from environmental exposures. The compositions may be used generally as deodorant compounds, as tanning agents, as skin protecting agents (especially with respect to damage from the sun and environmental exposures) and to beautify and rejuvenate skin.

Compositions according to the present invention may be administered by any conventional means known in the art, preferably by simply applying a cosmetic composition topically to the skin or nails of a subject in need. Pharmaceutical formulations include those suitable for oral, rectal, nasal, topical (including buccal and sub-lingual), or vaginal, but compositions which are administered by topical and/or transdermal route of administration directly at the site in the skin of the disease state or condition to be treated are clearly preferred. These may take the form of creams, oils, lotions, liquids and the like for application to the skin of a subject to be treated. Compositions according to the present invention may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives. When desired, the above described formulations may be adapted to provide sustained release characteristics of the active ingredient(s) in the composition using standard methods well-known in the art.

Cosmetic topical compositions for use in the present invention comprise at least one cosmetic additive compound as described herein, optionally in combination with an additional active agent (such as an anti-acne or other agent as described herein), further in combination with at least one additional cosmetic additive selected from a solvent (e.g. alcohol or other water compatible cosmetically acceptable solvent, such as ethanol, isopropanol, (poly)ethylene glycol and/or propylene glycol), a water incompatible solvent, emollients, humectants, oils (polar and non-polar which may provide oil-in-water or water-in-oil emulsions), conditioning agents, surfactants, thickeners/thickening agents, stiffening agents, emulsifiers, medicaments, fragrances, preservatives, deodorant components, anti-perspirant compounds, skin protecting agents, pigments, dyes, coloring agents, preservatives and mixtures thereof, among others. Each of these components is pharmaceutically acceptable or cosmetically acceptable and is known in the cosmetics and formulations arts.

The term "oil" is used throughout the specification to describe any of various lubricious, hydrophobic and combustible substances obtained from animal, vegetable and mineral matter. Oils for use in the present invention may include petroleum-based oil derivatives such as purified petrolatum and mineral oil. Petroleum-derived oils include aliphatic or wax-based oils, aromatic or asphalt-based oils and mixed base oils and may include relatively polar and non-polar oils. "Non-polar" oils are generally oils such as petrolatum or mineral oil or its derivatives which are hydrocarbons and are more hydrophobic and lipophilic compared to synthetic oils, such as esters, which may be referred to as "polar" oils. It is understood that within the class of oils, that the use of the terms "non-polar" and "polar" are relative within this very hydrophobic and lipophilic class, and all of the oils tend to be much more hydrophobic and lipophilic than the water phase which is used in the present invention.

In addition to the above-described oils, certain essential oils derived from plants such as volatile liquids derived from flowers, stems and leaves and other parts of the plant which may include terpenoids and other natural products including triglycerides may also be considered oils for purposes of the present invention.

Petrolatum (mineral fat, petroleum jelly or mineral jelly) and mineral oil products for use in the present invention may be obtained from a variety of suppliers. These products may range widely in viscosity and other physical and chemical characteristics such as molecular weight and purity. Preferred petrolatum and mineral oil for use in the present invention are those which exhibit significant utility in cosmetic and pharmaceutical products. Cosmetic grade oils are preferred oils for use in the present invention.

Additional oils for use in the present invention may include, for example, mono-, di- and tri-glycerides which may be natural or synthetic (derived from esterification of glycerol and at least one organic acid, saturated or unsaturated, such as for example, such as butyric, caproic, palmitic, stearic, oleic, linoleic or linolenic acids, among numerous others, preferably a fatty organic acid, comprising between 8 and 26 carbon atoms). Glyceride esters for use in the present invention include vegetable oils derived chiefly from seeds or nuts and include drying oils, for example, linseed, iticica and tung, among others; semi-drying oils, for example, soybean, sunflower, safflower and cottonseed oil; non-drying oils, for example castor and coconut oil; and other oils, such as those used in soap, for example palm oil. Hydrogenated vegetable oils also may be used in the present invention. Animal oils are also contemplated for use as glyceride esters and include, for example, fats such as tallow, lard and stearin and liquid fats, such as fish oils, fish-liver oils and other animal oils, including sperm oil, among numerous others. In addition, a number of other oils may be used, including $C_{12}$ to $C_{30}$ (or higher) fatty esters (other than the glyceride esters, which are described above) or any other acceptable cosmetic emollient.

Preferred oils for use in the present invention include petrolatum, mineral oil or mixtures of petrolatum and mineral oil where the amount of petrolatum to mineral oil (on a weight/weight basis) ranges from about 1:20 to about 10:1, preferably about 1:5 to about 5:1, more preferably about 1:3 to about 1:1, depending upon the end use of the emulsion composition. The inclusion of petrolatum and/or mineral oil and/or the ratio of petrolatum to mineral oil in the present compositions will greatly influence the final viscosity of the water-in-oil compositions according to the present invention.

The terms "emulsion" and "water-in-oil emulsion" and "oil-in-water emulsions are used to describe certain cosmetic compositions according to the present invention. An "emulsion" according to the present invention is a cream or lotion which is generally formed by the suspension of a very finely divided liquid, in this case water, in another liquid, in this case, an oil, or an oil within water as otherwise described herein. In the present invention, an emulsion is formed when the water phase is compatibilized in the oil phase, such that the water phase becomes "hidden" within the oil phase or the oil phase becomes hidden within the water phase. While not being limited by way of theory, it is believed that in the water-in-oil emulsion compositions according to the present invention, the oil phase produces a liposome- or encapsulation-like structure or a related structure surrounding water and/or the water phase, with the reaction product of an emulsifier serving to enhance the formation of the liposome-like structure and consequently, the emulsion composition. The term emulsion is used to distinguish the present compositions from compositions which contain at least two distinct phases, i.e., an oil phase and a water phase.

The term "thickeners/thickening agents" refers to a substance which can increase the viscosity of a liquid without substantially changing its other properties. Thickeners may also improve the suspension of other ingredients or emulsions which increases the stability of the cosmetic product. Some thickening agents are also gelling agents (gellants) forming a gel, dissolving as a colloid and forming a weakly cohesive internal structure. Other gellants act as thixotropic agents which thicken upon settling.

Compositions according to the present invention also optionally include an additional bioactive agent, such as an anti-acne compound (e.g. peroxides such as hydrogen peroxide and benzoyl peroxide, dialkyl peroxides, peresters, inorganic peroxides, percarbonates, triclosan, quaternary compounds, retinoids such as adapalene, isotretinoin, tretinoin, pharmaceutically acceptable salts and esters thereof and the like and mixtures thereof, among others), vitamin C, vitamin E, vitamin A, coenzyme Q, *Aloe vera* and other agents which are useful to enhance the appearance of skin. In certain embodiments, cosmetic compositions comprise at least two of the above-described compounds.

In the pharmaceutical aspect according to the present invention, the compound(s) according to the present invention is formulated preferably in admixture with a pharmaceutically acceptable carrier. In general, it is preferable to administer the pharmaceutical composition topically and in certain instances orally, but certain formulations also may be administered via other parenteral routes, such as transdermal, buccal, subcutaneous, suppository or other route, including via inhalation or intranasally. Topical routes of administration are preferred, but these tend to be formulated as cosmetic compositions, for example as oils, creams, lotions, liquids, roll-ons and the like. Oral dosage forms are preferably administered in tablet or capsule (preferably, hard or soft gelatin) form. Of course, one of ordinary skill in the art may modify the formulations within the teachings of the specification to provide numerous formulations for a particular route of administration without rendering the compositions of the present invention unstable or compromising their therapeutic activity.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol or sorbitan esters, microcrystalline cellulose, aluminum metahydroxide, bentonite, agar-agar, or tragacanth, or mixtures of these substances, and the like.

Compositions for rectal or vaginal administration, where applicable, can be prepared by mixing an active agent and any additional compounds with suitable non-irritating excipients or carriers such as cocoa butter, polyethylene glycol or a suppository wax, which are solid at ordinary room temperature, but liquid at body temperature, and therefore, melt in the rectum or vaginal cavity and release the active compound. These components may also be used to provide roll-on compositions for application to the skin of a subject to be treated.

Cosmetic compositions for topical administration include ointments, powders and sprays, in addition to oils, creams lotions and roll-ons. In addition to active compounds, cosmetic compositions include for example, at least one additional cosmetic additive selected from a solvent (e.g. alcohol or other water compatible cosmetically acceptable solvent), a water incompatible solvent, emollients, humectants, oils (polar and non-polar which may provide oil-in-water or water-in-oil emulsions), conditioning agents, surfactants, thickeners/thickening agents, stiffening agents, emulsifiers, medicaments, fragrances, preservatives, deodorant components, anti-perspirant compounds, skin protecting agents, pigments, dyes, coloring agents, preservatives and mixtures thereof, among others.

Generally, dosages and routes of administration of the pharmaceutical compositions and therapeutic compounds described herein are determined according to the size and condition of the subject, according to standard practice. Dose levels employed can vary widely, and can readily be determined by those of skill in the art. Typically, amounts in the milligram up to gram quantities are employed, depending the area affected, the effect intended, the severity of the disease and the age of the subject.

The dosage administered pursuant to the present invention is an effective amount for producing an intended result and will vary depending upon known factors such as the penetration kinetics and/or pharmacodynamic characteristics of the particular agent and the ability of the agent to penetrate the tissue to which the composition has been administered or applied, as well as the age, health, and weight of the recipient; nature and extent of symptoms, kind of concurrent treatment, frequency of treatment, and the effect desired.

Usually a daily dosage of active compound can be about 0.01 to 500 milligrams per kilogram of body weight or more, often 0.1 milligrams to 250 milligrams per kilogram of body weight. Ordinarily, 0.5 to 50, and often 1 to 25 milligrams per kilogram per day given in divided doses 1 to 6 times a day, as needed or in sustained release form (often, transdermal administration) is effective to obtain desired results.

The active compounds may be used at a concentration of 0.01 to 99.9 weight percent of the formulation, or in some cases a concentration of 0.001 to 99.9 weight percent of the formulation. Often the active compound is included in the composition in amounts ranging from 0.01 wt % to up to 10 wt % or more, often 0.1 wt % to about 5 wt %. Cosmetic compositions for application directly to the skin are preferably formulated in lotions, creams, salves or liquids. Many of these compositions comprise water-in-oil or oil-in-water emulsions with the active compounds being included therein. The topical formulation dosage with vary with the amount applied to the area of tissue to be treated. In contrast, the pharmaceutical formulation, when used, is preferably in unit dosage form. The unit dosage form can be a capsule or tablet itself, or the appropriate number of any of these. The quantity of active compound in a unit dose of composition may be varied or adjusted from about 0.05 to several grams, often 0.1 to about 1000 milligrams or more or about 1 milligram to 500 milligrams according to the particular treatment involved. Compositions (dosage forms) suitable for internal administration contain from about 1 milligram to about 1000 milligrams of active compound per unit. In these pharmaceutical compositions the active compound will ordinarily be present in an amount of about 0.5-95% by weight based on the total weight of the composition.

EXAMPLES

Exemplary Compositions for Deodorant (Solid or Semi-Solid)

Example 1 (Aluminum Free Formula)

Beeswax, cocoa butter, coconut oil, shea butter, vitamin E (tocopherol), sunflower seed oil, zinc oxide This or any other generic deodorant base will be supplemented with inhibitors of cAMP efflux (ICE) (at least one) of artemisinin, artemether, artesunate, dihydroartemisinin, patulin, pyrithione zinc, parthenolide, quinalizarin, clioquinol, cryptotanshinone, harmalol, or other compounds according to the chemical structure listed above.

The following composition can be also supplemented with sweet almond oil, rosemary leaf extract, rosehip seed oil, cypress oil, tea tree leaf oil or any other pharmaceutically and/or cosmetically acceptable aroma/scents/botanicals/coloring to provide desired scents/color for personal care products.

Example 2 (Aluminum Free Formula with Safflower Oil and Sodium Bicarbonate, Safflower Grows Along Rio Grande Valley in New Mexico)

Beeswax, coconut oil, safflower oil, shea butter, arrowroot powder, vitamin E (tocopherol), baking soda (sodium bicarbonate)

Supplemented with inhibitors of cAMP efflux (ICE) (at least one) of artemisinin, artemether, artesunate, dihydroartemisinin, patulin, pyrithione zinc, parthenolide, quinalizarin, clioquinol, cryptotanshinone, harmalol, or any other ICE compounds according to the chemical's list and chemical structures listed herewith.

Example 3 (Aluminum Free Formula with Olive Oil)

Beeswax, coconut oil, olive oil, shea butter, arrowroot powder, vitamin E (tocopherol)

Supplemented with inhibitors of cAMP efflux (ICE) (at least one) of artemisinin, artemether, artesunate, dihydroartemisinin, patulin, pyrithione zinc, parthenolide, quinalizarin, clioquinol, cryptotanshinone, harmalol, or any other ICE compounds according to the chemical's list and chemical structures listed herewith.

Exemplary Compositions for Body, Hand, Heel and Foot Lotion

Example 1

Water, propylene glycol, mineral oil, stearic acid, cetyl alcohol, ethylenediaminetetraacetic acid, glyceryl stearate, *Aloe vera* gel, triethanolamine, white petrolatum (petroleum jelly), polydimethylsiloxane (dimethylpolysiloxane, dimethicone) propylparaben or methylparaben, 5-ureidohydantoin (allantoin), polyacrylic acid (carbomer), diazolidinyl urea or iodopropynyl butylcarbamate or any other pharmaceutically and/or cosmetically acceptable anti-bacterial or antimicrobial preservative.

This generic body, hand, heel and foot lotion base or any modification of thereof will be supplemented with inhibitors of cAMP efflux (ICE) (at least one) of artemisinin, artemether, artesunate, dihydroartemisinin, patulin, pyrithione zinc, parthenolide, quinalizarin, clioquinol, cryptotanshinone, harmalol, or any other ICE compounds according to the chemical's list and chemical structures listed herewith.

Additionally, if desired the following composition can be also supplemented with sweet almond oil, rosemary leaf extract, rosehip seed oil, cypress oil, tea tree leaf oil or any other pharmaceutically and/or cosmetically acceptable aroma/scents/botanicals to provide desired scents/coloration for personal care products.

Scientific Rationale for the Use of ICE in Deodorant and Cosmetic Formulations

In 2013, the Avon Longitudinal Study of Parents and Children (ALSPAC: ~17,000 individual population cohort) reported data on deodorant usage. The authors showed that a significant fraction of the Eastern Asian population never used deodorant or used it very infrequently [5]. This was associated with the rs17822931, a single-nucleotide polymorphism (SNP) located in the ABCC11 gene. The SNP rs17822931 (GS38A; G180R) in ABCC11 was first discovered as a genetic variant that determines the type of earwax in humans [6]. The wild-type of ABCC11 is associated with brownish, sticky, wet-type earwax and axillary osmidrosis, a condition that is characterized by an unpleasant odor from the products of the microbial degradation of skin excreta [7, 8]. The G180R and a 27-bp deletion in the ABCC4 C-terminus are related to the formation of dry-type earwax. The G180R variant lacks the N-linked glycosylation that is necessary for stable protein expression, and therefore it undergoes rapid proteasomal degradation [8]. As a result, the absence of the functional ABCC11 transporter in cells of apocrine glands in individuals with rs17822931 leads to a diminished secretion of malodorous compound precursors. This results in virtually "odorless sweat". According to the ALSPAC study "homozygotes for the rs17822931 A allele within ABCC11 are almost 5-fold less likely to use deodorant than GG homozygotes and heterozygotes for this SNP" [5]. This phenomenon is concentrated within East- and Northeast Asia, including Korea, China, Mongolia, and western Japan. The allele frequency of rs17822931 is very low in Europeans and Africans who are the most avid deodorant users.

In addition to odorous sweat compound precursors, the ABCC11 transporter is capable of transporting a large number of other substrates including cyclic nucleotides (cAMP and cGMP) [9]. The identification of ICE compounds [1-4] created a tool for the down-modulation of ABCC11 activity. Since a mutated ABCC11 transporter in Eastern Asians carrying rs17822931 SNP creates no known undesirable effects, with the exception of the odorless sweat and the dry-type earwax, the use of these compounds in cosmetic formulations is likely very safe. Moreover, inhibiting the ABCC11 transporter for the purpose of decreasing an unwanted body odor will mimic the natural odorless sweat mechanism (rs17822931 SNP) that has been present in the Eastern Asian population for ~40,000 years. A recent genome-wide association study in Japanese females that identifies a relationship between skin-related traits and ABCC11 genetic variants suggests that ICE can also be beneficial as part of skin cosmetic formulations [10].

Scientific Rationale for the Use of ICE as Artificial Tanning Agents

It has long been known that modulation of the cAMP pathway can regulate melanogenesis [11]. The up-regulation of cytosolic cAMP levels using the stimulator of the adenylyl cyclase activity (forskolin) [12], inhibition of cAMP hydrolysis with phosphodiesterase inhibitor [13] or by the activation GalphaS-coupled GPCR [14] can all stimulate melanin synthesis and skin pigmentation/darkening. Because ICE increase cAMP signaling through an entirely different mechanism, we have unexpectedly discovered that these compounds could similarly increase melanogenesis, and thus generate an artificial tanning effect in the absence of UV exposure.

REFERENCES CITED

1. Chigaev, A., L. A. Sklar. and D. Perez, *Method for cancer cell reprogramming* 2016. U.S. Pat. No. 9,314,460 B1 (Ser. No. 14/249,150).
2. Chigaev, A., L. A. Sklar, and D. Perez, *Method for cancer cell reprogramming.* 2018. U.S. Pat. No. 10,039,771 B2 (Ser. No. 15/131,358).
3. Perez, D., et al., *A High-Throughput Flow Cytometry Assay for Identification of Inhibitors of 3'5'-Cyclic Adenosine Monophosphate Efflux.* Methods Mol Biol, 2016. 1439: p. 227-44.
4. Perez, D. R., et al., *Cyclic AMP efflux inhibitors as potential therapeutic agents for leukemia.* Oncotarget, 2016. 7(23): p. 33960-82.
5. Rodriguez, S., et al., *Dependence of deodorant usage on ABCC11 genotype: scope for personalized genetics in personal hygiene.* J Invest Dermatol, 2013. 133(7): p. 1760-7.
6. Yoshiura, K., et al., *A SNP in the ABCC11 gene is the determinant of human earwax type.* Nat Genet, 2006. 38(3): p. 324-30.
7. Nakano, M., et al., *A strong association of axillary osmidrosis with the wet earwax type determined by genotyping of the ABCC11 gene.* BMC Genet, 2009. 10: p. 42.
8. Toyoda, Y., et al., *Earwax, osmidrosis, and breast cancer: why does one SNP (538G>A) in the human ABC transporter ABCC11 gene determine earwax type?* FASEB J, 2009. 23(6): p. 2001-13.
9. Guo, Y., et al., *MRP8, ATP-binding cassette C11 (ABCC11), is a cyclic nucleotide efflux pump and a resistance factor for fluoropyrimidines 2',3'-dideoxycytidine and 9'-(2'-phosphonylmethoxyethyl)adenine.* J Biol Chem, 2003. 278(32): p. 29509-14.
10. Endo, C., et al., *Genome-wide association study in Japanese females identifies fifteen novel skin-related trait associations.* Sci Rep, 2018. 8(1): p. 8974.
11. D'Mello, S. A., et al., *Signaling Pathways in Melanogenesis.* Int J Mot Sci, 2016. 17(7).
12. Spry, M. L., et al., *Prolonged treatment of fair-skinned mice with topical forskolin causes persistent tanning and UV protection.* Pigment Cell Melanoma Res, 2009. 22(2): p. 219-29.
13. Zhang, X. et al., *PDE5 inhibitor promotes melanin synthesis through the PKG pathway in B16 melanoma cells.* J Cell Biochem, 2012. 113(8): p. 2738-43.
14. Natale, C. A., et al., *Sex steroids regulate skin pigmentation through nonclassical membrane-bound receptors.* Elife, 2016. 5.

The invention claimed is:

1. A method of treating body malodor and/or hyperhidrosis in a subject comprising administering to said subject a composition comprising an effective amount of a cAMP efflux inhibitor in combination with at least one additional cosmetic additive, wherein said cAMP efflux inhibitor is compound according to the chemical structure:

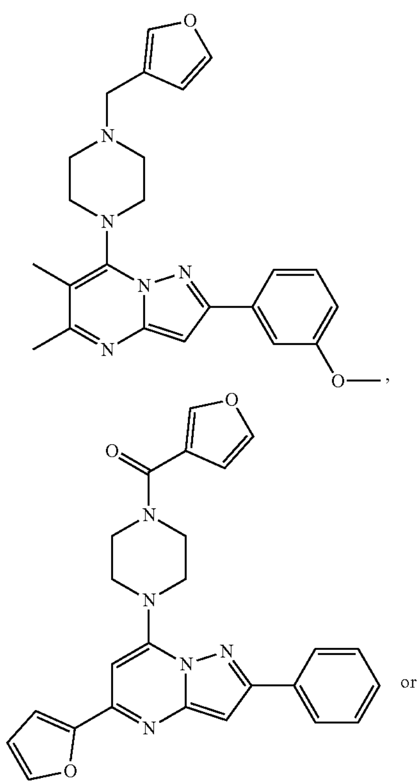

-continued

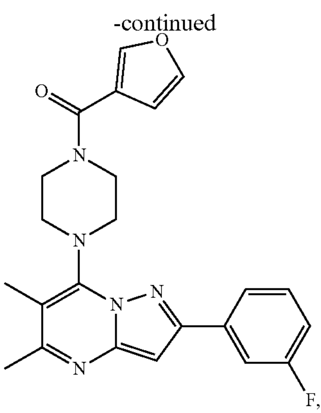

a pharmaceutically acceptable salt or stereoisomer thereof, or a mixture thereof; and said at least one cosmetic additive is water, an alcohol or other water compatible cosmetically acceptable solvent, a water incompatible solvent, an emollient, a humectant, an oil, a conditioning agent, a surfactant, a thickener/thickening agent, a stiffening agent, an emulsifier, a medicament, a fragrance, a preservative, a deodorant component, an antiperspirant compound, a skin protecting agent, a pigment, a dye, a coloring agent, a preservative or a mixture thereof.

2. The method according to claim 1 wherein said composition comprises at least one deodorant or antiperspirant compound.

3. The method according to claim 2 wherein said deodorant compound is triclosan or cyclomethicone and said antiperspirant compound is an aluminum salt.

4. The method according to claim 3 wherein said aluminum salt is aluminum chlorhydrate, aluminum formate, aluminum zirconium tetrachlorhydrex glycine or a mixture thereof.

* * * * *